US00PP24299P2

(12) United States Plant Patent
Jeske et al.

(10) Patent No.: US PP24,299 P2
(45) Date of Patent: Mar. 11, 2014

(54) HOP PLANT NAMED 'CALYPSO'

(50) Latin Name: ***Humulus lupulus* L.**
Varietal Denomination: Calypso

(75) Inventors: Roger D. Jeske, Yakima, WA (US); Paul D. Matthews, Yakima, WA (US)

(73) Assignee: S.S. Steiner, Inc., New York, NY (US)

( * ) Notice: Subject to any disclaimer, the term of this patent is extended or adjusted under 35 U.S.C. 154(b) by 106 days.

(21) Appl. No.: 13/385,098

(22) Filed: Feb. 1, 2012

(51) Int. Cl.
*A01H 5/00* (2006.01)

(52) U.S. Cl.
USPC ..... Plt./236

(58) Field of Classification Search
USPC ..... Plt./236
See application file for complete search history.

*Primary Examiner* — Howard Locker
(74) *Attorney, Agent, or Firm* — Hayes Soloway P.C.

(57) ABSTRACT

A new and distinct aroma variety of hop, *Humulus lupulus* L., named 'CALYPSO' is characterized by its large yield, unique aroma and resistance to hop powdery mildew.

3 Drawing Sheets

BACKGROUND OF INVENTION

The flowers (cones) of the female hop plant, *Humulus lupulus* L, are used in the making of beverages, especially beer, as a flavoring and processing component. Hops contribute towards the bitterness and aroma in beer as well as foam quality, flavor, and taste stability. Various hop varieties have various special uses in the beer brewing industry. Aroma hops are used to impart flavors by virtue of the distinct profiles of their essential oils and terpene alcohols, among other compounds, as well as to supply bitter flavors based on specific contents of bitter acids, namely, terpenophenolics, mostly humulones. Examples of aroma hops are the cultivars known as variety 'Willamette' (non-patented), variety 'Centennial' (non-patented), variety 'Sterling' non-patented), variety 'Cascade' (non-patented), and variety 'Glacier' (non-patented). Many aroma varieties are susceptible to fungal pathogens, in particular powdery mildew, and otherwise exhibit less than ideal agronomic traits. The present invention relates to a novel hop variety which retains the good "aroma" qualities of the above mentioned varieties, yet is unique by having: a higher percentage of alpha-acids, powdery mildew resistance, downy mildew tolerance, significant improvements in agronomic traits and a distinctly fruity aroma.

Hop plants, hop cones, male hop flowers, hop plant parts, hop tissue cultures and hop extracts also have bioactive properties: including anti-microbial, anti-cancer, anti-osteoporosis, antioxidative, anti-inflammatory, antibiotic, soporific, anti-androgenic, and pro-estrogenic activities, among others; which may be used in herbal remedies, in antimicrobial preparations for food, fodder, food fermentation, food process, animal husbandry; or in non-food uses, such as composting, bio-fuel processing, fermentation process, water treatment, animal bedding and phytoremediation; and uses in cosmetics, in nutraceutical and in pharmaceutical applications and in research thereof. Examples of activities and non-beverage uses are included herein by references: J Hazard Mater. Apr. 26; 91(1-3):95-112; Mol Cancer Ther. Sep; 1(1 1):959-69; Phytochemistry. May; 65(IO):1317-30; U.S. Pat. No. 6,423,317 (2002); U.S. Pat. No. 6,623,775 (2003).

Agricultural end-product users, growers, handlers and processors of hops, of hop plants, of hop tissues and of hop products use hops and are affected by the agronomic, developmental, morphological, chemical and physical properties that vary among unique and distinct asexually reproduced varieties, Users of hops are also interested in new combinations or mixtures of hop cultivars that improve the quality of beverage flavor and process and storage properties. This invention relates to a novel asexually produced hop variety, named 'CALYPSO', invented in a planned and systematically executed breeding program.

SUMMARY OF INVENTION

This invention relates to a new genetically, chemically, and morphologically distinct variety of hop selected from among the multitude of hop plants resulting from a controlled cross-pollination during the summer of 2002. The cross-pollination was between a proprietary non-patented female hop referred to as '98005' with a proprietary, non-patented male hop plant 'FA-9901m'.

The cross-pollination resulting in 'CALYPSO' was performed in 2002 by Roger Jeske in a field in Prosser, Wash. During 2003 seeds collected from the cross-pollination were germinated and then screened for powdery mildew resistance in a greenhouse in Prosser, Wash. These seedlings, which originated from seed, were planted in a field nursery and further screened for gender, vigor, cone type, and disease susceptibility with the best genotypes being advanced to a single hill hop nursery during the spring of 2004. Mr. Jeske discovered the 'CALYPSO' variety during the summer of 2005 among the numerous hop genotypes growing in a single hill hop nursery in Prosser, Wash. These hop genotypes growing in the single hill hop nursery were grown in a 3.5 foot by 14 foot spacing on twine attached to an 18 foot trellis system. Field observations and chemical analysis of the mature hop during 2005 demonstrated vigorous growth, no powdery mildew in the leaves and cones, an exceptional large firm cone, 16-17% alpha-acid, a pleasant yet distinct aroma and flavors, and a high percentage of total oils. Cones were large, numerous and easy to pick with no shatter. Vigor was excellent and the yield potential appeared to be exceptional, based on the breeder's experience. There was no harvest of the single hill 'CALYPSO' in 2005.

In March and April, 2006, 'CALYPSO' was asexually propagated true to type from soft wood cutting in greenhouses at Prosser, Wash. Rhizomes from the original single hill plant of 'CALYPSO' were dug, divided and planted into greenhouse grown containers. Softwood cuttings were taken from these original containers until approximately 48 softwood-cutting plants were made. These plants constituted the first asexual reproduction of the 'CALYPSO' variety and are the second generation. They were planted and grown at two distinct geographical locations with no powdery mildew observed during 2006 or any subsequent years. These two small scale trials consisted of a multi-hill planting (14 plants) in a field located in Prosser, Wash. and a multi-hill planting (16 plants) in afield located in Sunnyside, Wash. These trials were subjected to standard agronomic, cultural and management practices for the purposes of determining adaptability of 'CALYPSO' to various soils, geographical locations, and cultural practices.

During 2006, 2007, 2008, 2009, 2010 and 2011, second-generation plants in the two small-scale trials were observed for disease, sampled for chemical analysis, and harvested for yield evaluations. Results from the test plots provided additional information supporting the disease resistance, yield potential, alpha-acids, beta-acids, total oils, and unique aroma profile made from the original 'CALYPSO' plant (first generation) selected in 2005. These second-generation, small-scale trials confirmed that 'CALYPSO' has powdery mildew disease resistance, an excellent yield, a distinct apple/pear aroma, 1.5-2.5% total oils, and alpha-acids values ranging from 14-17%. Harvest of second-generation plants of 'CALYPSO' grown in these two small-scale trials yielded a range of 2,400-3,000 pounds per acre during 2007, 2008, 2009, 2010 and 2011 harvests.

In 2007, the second asexual reproduction of the 'CALYPSO' variety took place. Rhizomes from the second-generation rootstock from the multi-hill plants were collected, divided and planted into greenhouse grown containers. Softwood cuttings were taken from these containers until approximately 2,000 asexual clone plants were produced. These third-generation plants were planted into a one acre plot in a field near Prosser, Wash. in a 3.5 foot by 14 foot configuration (889 hills per acre), with two softwood cuttings planted per hill. This one acre trial was subjected to standard agronomic, cultural and management practices for the purposes of determining commercial harvest ability, yield, chemical characteristics, and process ability. Third-generation plants were sampled for chemical analysis and harvested for yield evaluations. Results from this third generation large-scale test plot provided additional information supporting the powdery mildew resistance, large yield, and unique fruity aroma characteristics of 'CALYPSO'. The 2008 harvested test plot of mature 'CALYPSO' plants produced 3,042 lbs/acre. Bale samples showed an alpha-acid of 16.3% and beta-acid of 5.9% (American Society of Brewing Chemists spectrophotometric method). The 2009 harvested test plot of mature 'CALYPSO' plants produced an average of 2,704 lbs/acre. Bale samples showed an alpha-acid of 14.0% and beta-acid of 5.7% (American Society of Brewing Chemists spectrophotometric method).

In 2008, the multi-hill plots of 'CALYPSO' that were being grown at Prosser and Sunnyside, Wash., were expanded to two other distinct geographical locations in Idaho's Treasure Valley and Oregon's Willamette Valley. These two small scale trials consisted of a multi-hill planting (14 plants) located in a field near Wilder, Id. and a multi-hill planting (20 plants) located in afield near Silverton, Oreg. These trials were subjected to standard agronomic, cultural and management practices for the purposes of determining yield, disease tolerance, chemical characteristics, and adaptability of 'CALYPSO' to various soils, geographical locations, day lengths, and cultural practices. During 2009 and 2010, second-generation plants in small-scale trials in Idaho and Oregon were observed for disease, for chemical content, and for yield. Results from the Idaho and Oregon test plots provided additional information supporting and confirming the powdery mildew disease resistance, large yield, unique fruity aroma, and alpha-acids contents of 14-17%. The harvest of mature, third-generation plants of 'CALYPSO' grown in multi-hill plantings in Idaho and Oregon during 2009 and 2010 yielded between 2,700 pounds per acre and 3,100 pounds per acre.

Based on agronomic and chemical evaluations over a number of growing seasons and geographic locations, both secondary and tertiary clones (second and third generations) of 'CALYPSO' exhibited genetic stability with respect to its novel characteristics of a distinct fruity (apple/pear) aroma, powdery mildew resistance in Washington, Oregon and Idaho, good vigor with an large yield (averaging 2,800 pounds per acre), 1.5-2.5% total oils, and 14-17% alpha-acids. This is in contrast to the non-patented female parent, '98005', which has a non-distinct aroma, is susceptible to powdery mildew, has a poor yield, and a lower alpha acid content. 'CALYPSO' has consistently yielded 40-50% more cone weight per acre than its non-patented female parent '98005'.

Observations, evaluations and testing of the 'CALYPSO' variety's agronomic, morphological, physical, and chemical properties were carried out by or directed by the inventor, Roger Jeske.

The variety 'CALYPSO' is early/mid maturing and is usually ready to pick by September 1-10th. The large firm and ovoid shaped cones of this variety are easy to mechanically pick and clean. The cones detach easily from stems with no shatter during commercial harvesting and drying.

In order to demonstrate genetic and phenotypic distinctiveness to closely related varieties, 'CALYPSO' is compared to its non-patented female parent '98005' and other agronomically important aroma varieties. The primary differences between the new 'CALYPSO' variety and '98005' (non-patented), 'Cascade' (non-patented), 'Centennial' (non-patented), 'Sterling' (non-patented), 'Glacier' (non-patented) and 'Chinook' (non-patented) is 'CALYPSO' has a higher yield (2,400-2,800 lbs/ac), higher alpha-acid percentage (14-17%), larger cones (340-400 mg), higher CoH (38-42%), as well as, a distinct fruity aroma. Similarities between 'CALYPSO', 'Cascade' (non-patented), 'Centennial' (non-patented), and 'Chinook' (non-patented) include early/mid maturity, total oils of 1.5-2.5 ml/100 g, and a humulene/caryophyllene ratio of 2.0:2.5.

The detailed botanical description and drawings herein below allow distinction of the variety from related varieties.

BRIEF DESCRIPTION OF THE DRAWINGS

Accompanying photographs illustrate the leaves, cones and growth habit of the new 'CALYPSO' variety just prior to harvest from a 3rd year planting.

GENERAL BOTANICAL DESCRIPTION OF THE VARIETY

Figure 1:
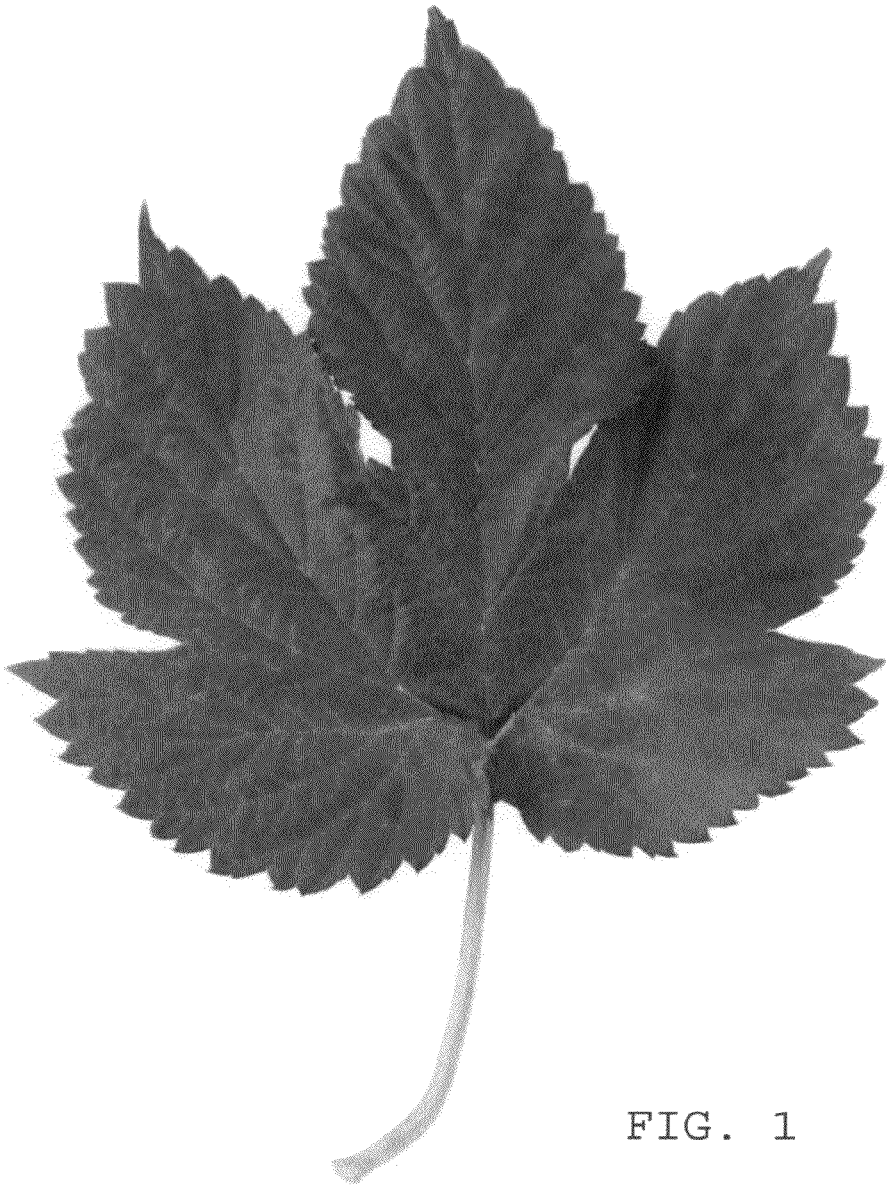
FIG. 1 depicts a close up of mature main vine leaf.
Figure 2:
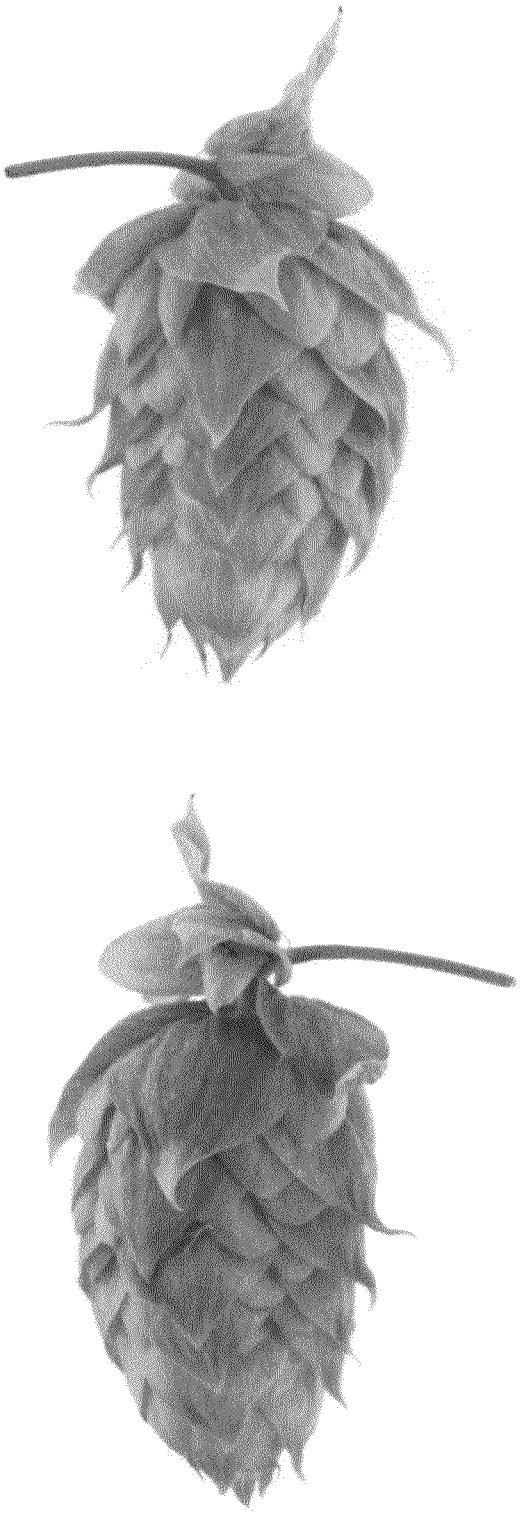
FIG. 2 depicts a close up of whole cones.
Figure 3:
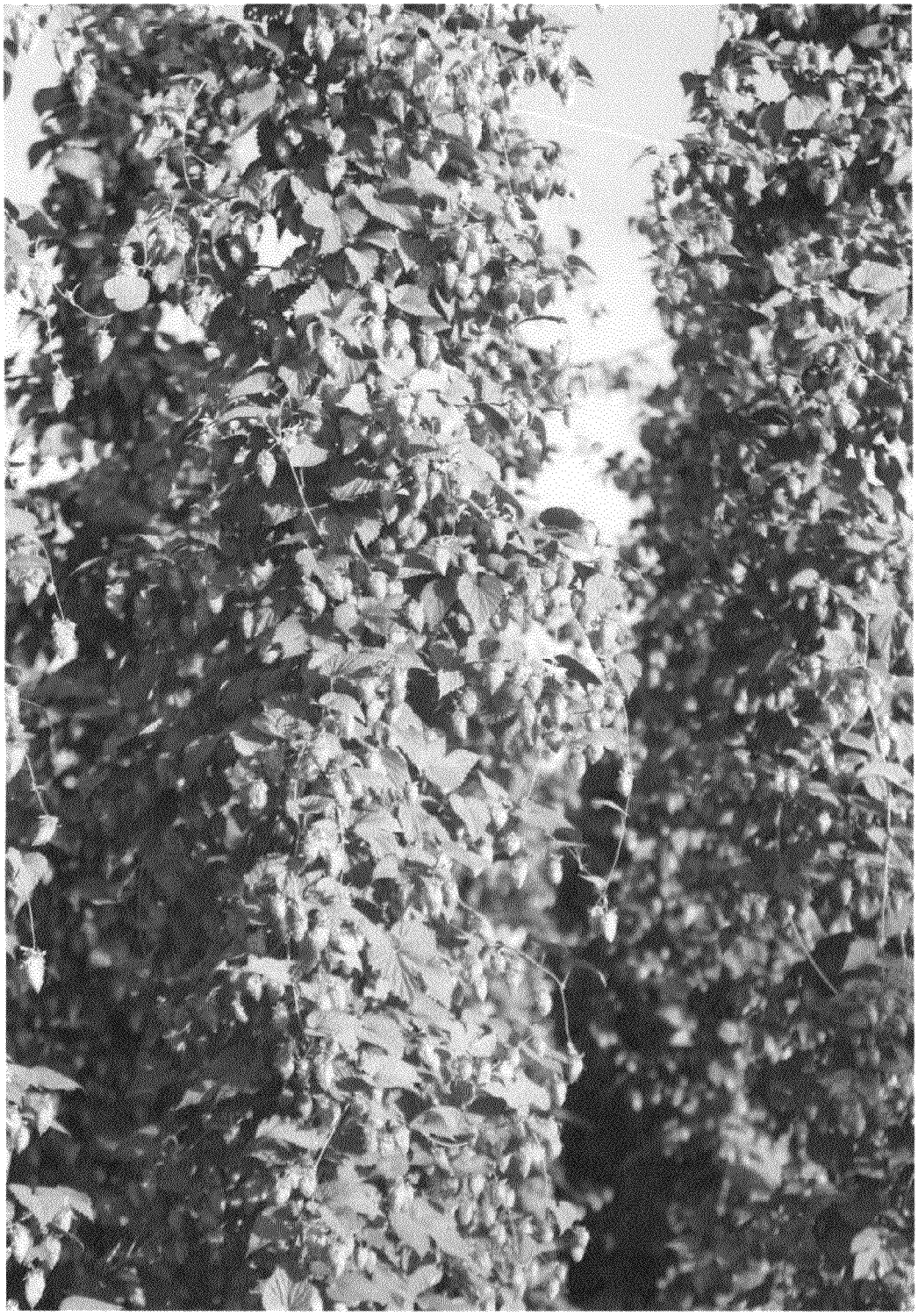
FIG. 3 depicts the appearance of the plants and cones as they are growing in the field on a high trellis (18 foot) approaching harvest time.

This description provides information on agronomic, morphological, chemical and processing characteristics of the new variety that are used in distinction and identification of a new hop variety and its parts and products by practitioners of the industries that use hops as described herein above.

General information on the botanical characteristics and cultural aspects of hop plants as they relate to agronomics, breeding and food use are particularly well discussed in the prior art, especially, U.S. Plant Pat. Nos. 10,956; 13,132; 18,039; 18,602; 20,200; and 20,227 and the literature; "Steiner's Guide to American Hops Book III", 1986; "Hops" Published by Chapman and Hall, 1991. Detailed botanical information below of the present variety is directly comparable to the prior art, as contained by reference herein.

DETAILED BOTANICAL DESCRIPTION OF THE VARIETY

Following is a detailed description of the botanical and analytical chemical characteristics of the new variety. The information for this botanical description was either collected or verified during the growing seasons of 2005, 2006, 2007, 2008, 2009, 2010 and 2011.

Botanical characteristics, and to a lesser degree the analytical characteristics, are somewhat dependent on cultural practices and climatic conditions and can vary with location or year:

1. Parentage: A hop plant originating from a controlled cross-pollination between a proprietary non-patented female hop plant referred to as '98005' with a proprietary, non-patented male hop plant referred to as 'FA-9901m'.
2. Locality where grown and observed: North of Prosser, Wash.; south of Sunnyside, Wash.; north of Wilder, Id.; and northwest of Silverton, Oreg.
3. Agronomic factors: Dates of first and last harvest are approximately September 1st and September 10$^{th}$. Shoots of 'CALYPSO' emerge from winter dormancy about one week later than commercial varieties 'Cascade' and 'Centennial' (both non-patented). Emergence is typically by March 25$^{th}$ and the initial stem growth is fairly slow like cultivars 'Cascade' or 'Galena' (both non-patented). 'CALYPSO' shows average vigor after spring pruning when compared to other commercial varieties. Plants were pruned and sprayed using conventional hop cultivating practices. The initial stem color and leaves during April are purple to violet (RHS N77B). During the late summer, main vine stems are green (RHS 145A). The main vine sterns of 'CALYPSO' are round in cross section shape with no pronounced stripes. The inflorescence of 'CALYPSO' begins to appear in the middle of July and mature during the first week of September. Cone shape is fairly uniform in the 'CALYPSO' variety. The hop cones of 'CALYPSO' are well adapted to mechanical harvest because of their large size, ovoid shape, and they roll on dribble belts, making cleaning easy. The firm semi-dense cones do not shatter during harvest. In the following description color code designations are by reference to The R.H.S. Colour Chart, 4$^{th}$ Edition, provided by The Royal Horticultural Society of Great Britain.
4. Plant characteristics:
   - *Plant.*—Vigorous, climbing vine.
   - *Plant shape.*—Columnar.
   - *Bine color.*—Green (RHS 145A).
   - *Bine stripe.*—None.
   - *Bine inter-node length* (*at 6' high — measured from the ground*).—28-32 cm.
   - *Bine diameter* (*at 6 feet high*).—0.8-1.0 cm.
   - *Bine length.*—18-21 feet.
   - *Petiole length.*—10-14 cm.
   - *Petiole color.*—Green (RHS 145B).
   - *Petiole shape.*—Slightly channeld (flat upper surface).
   - *Leaf arrangement.*—Opposite.
   - *Leaf shape.*—Cordate.
   - *Leaf color.*—Upper surface — dark green — (RHS N137A).
   - *Leaf color.*—Lower surface — green — (RHS 147B).
   - *Mature leaf width.*—18-21 cm.
   - *Mature leaf length.*—20-21 cm.
   - *Number of main bine leaf lobes.*—Five (occasionally 3).
   - *Venation pattern.*—Netted (Palmately veined).
   - *Vein color.*—Green (RHS 146C).
   - *Leaf margin.*—Moderately dentate.
   - *Lateral length* (*at 6 feet high — measured from the ground*).—Ranging in size from 1.0-1.3 m.
   - *Internode length of lateral* (*at 6 feet high*).—18-24 cm.
   - *Stipule position.*—Outward-up, pointed.
   - *Stipule color.*—Green (RHS 145B).
5. Reproductive organs, cones, cone parts, seeds:
   - *Bract color.*—Yellow-green (RHS 146B).
   - *Bract tips shape.*—Sub-acute.
   - *Bract tip position.*—Slightly everted.
   - *Bract diameter.*—1.5-2.0 cm.
   - *Bracteole diameter.*—1.0-13 cm.
   - *Bracteole shape.*—Lanceolate.
   - *Bracteole color.*—Yellow-green (RHS 146D).
   - *Compactness.*—Firm semi-dense.
   - *Shape.*—Ovoid, square in radial section.
   - *Cone length.*—3.5-4.0 cm.
   - *Cone diameter at shoulder.*—2.0-2.5 cm.
   - *Cone tip shape.*—Tapered to a distinct point.
   - *Cone weight.*—340-400 mg.
   - *Strig.*—Compact.
   - *Lupulin glands.*—The cone of the present variety contains numerous lupulin glands. Yield per acre. — 2400-2800 pounds on average.
   - *Seeds.*—Highly variable in color and size depending on male parent.
   - *Date of maturity.*—Considered to be early-mid (September 1$^{st}$ to September 10$^{th}$) as compared to other common hop varieties grown in central Washington.
6. Chemical content of cones:
   - % *Alpha-acids* (*bale*).—13-16% (ASBC spectrophotometric method).
   - % *Beta-acids* (*bale*).—5-6% (ASBC spectrophotometric method). Alpha/beta ratio. — 2.5-3.0. Cohumulone "CoH" (% of alpha-acids). — 38-42%.
   - *Storage characteristics.*—30-35% transformation of alpha-acids after 6 months at 22 degrees C.
   - *Total oils* (*mls/100 g*).—1.5-2.5. Humulene (% of total oils). — 20-35%. Caryophyllene (% of total oils). — 9-15%.
   - *Humulene/caryophyllene ratio.*—2.0-2.5.
   - *Farnesene* (*% of total oils*).—<1.0%.
   - *Myrcene* (*% of total oils*).—30-45%.

7. Disease resistance: The variety 'CALYPSO' is resistant to the strains of powdery mildew fungus found in the Yakima Valley, Wash.: Treasure Valley, Id.; and Willamette Valley, Oreg. as of 2011, but since not all strains are present in the U.S. no future powdery mildew resistance can be assured. 'CALYPSO' appears to be tolerant to strains of *Verticillium wilt*, and the virus diseases found in the USA growing areas. 'CALYPSO' appears to be very tolerant to hop downy mildew.
8. Regional adaptation: The 'CALYPSO' variety is well adapted to the drier growing regions of Washington State and Idaho State specifically the Yakima Valley and the Treasure Valley. 'CALYPSO' was tested in the Willamette Valley of Oreg. in 2008, 2009 and 2010 and appears to be suitable to this area even with the higher humidity and the threat of downy mildew infections.
9. Ploidy: Hop variety 'CALYPSO' is diploid. The female parent is diploid and the 'male parent' is diploid.
10. Life expectancy: Indefinite, similar to other hop varieties.
11. Use: Flavoring and conditioning of beverages and foods and use as a vegetable. Constituent of herbal remedies, nutraceuticals, pharmaceuticals, drugs, ointments, antiseptic washes, and cosmetics for humans and animals. Constituent of fodder, bedding, compost, agricultural treatments, phytoremediation treatments, water and soil treatments, conditioning of fermentation and other industrial processes. Used in breeding novel hop varieties.
12. Propagation status: 'CALYPSO' rootstock and plant propagation material exists. Asexual plant propagation has been demonstrated.
13. Reproductive status: 'CALYPSO' is fertile and produces seeds upon pollination with male hop plants.

DISTINGUISHING CHARACTERISTICS

This new hop variety 'CALYPSO' can be distinguished from all other USA commercial aroma varieties by its combination of powdery mildew resistance, excellent yield, unique fruity aroma, large, semi-dense cones, high CoH, and higher alpha-acid % than other aroma varieties.

We claim:

1. A new and distinct aroma hop plant, named 'CALYPSO' as herein described and illustrated.

* * * * *